US008691710B2

(12) United States Patent
Bailey, III et al.

(10) Patent No.: US 8,691,710 B2
(45) Date of Patent: Apr. 8, 2014

(54) GROUP IV METAL COMPLEXES FOR METAL-CONTAINING FILM DEPOSITION

(75) Inventors: Wade Hampton Bailey, III, Emmaus, PA (US); Sergei Vladimirovich Ivanov, Schnecksville, PA (US); Xinjian Lei, Vista, CA (US); Moo-Sung Kim, Sungnam (KR)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 13/362,077

(22) Filed: Jan. 31, 2012

(65) Prior Publication Data

US 2013/0030191 A1 Jan. 31, 2013

Related U.S. Application Data

(60) Provisional application No. 61/440,469, filed on Feb. 8, 2011.

(51) Int. Cl.
*C07D 207/46* (2006.01)
*H01L 21/70* (2006.01)

(52) U.S. Cl.
USPC .......................................... 438/785; 548/523

(58) Field of Classification Search
USPC ........................................................ 548/523
See application file for complete search history.

(56) References Cited

U.S. PATENT DOCUMENTS

| 5,300,321 A | 4/1994 | Nakano et al. |
| 7,332,618 B2 | 2/2008 | Meiere |
| 2008/0081922 A1 | 4/2008 | Meiere et al. |

FOREIGN PATENT DOCUMENTS

| DE | 41 20 344 A1 | 1/1999 |
| WO | 2009/086263 A1 | 7/2009 |
| WO | 2009/155507 A1 | 12/2009 |
| WO | 2009/155520 A1 | 12/2009 |

OTHER PUBLICATIONS

Dias, et al. Document No. 140:42261, CAPLUS, 2003.*
R. Vann Bynum, Pyrrolyl complexes of the early transition metals. 3. Synthesis and crystal structure of (η5-C5H5)2Ti(η 1-NC4H2Me2)2 and (η5-C5H5)2Zr(η 1-NC4H2Me2)2, 1986, Can. J. Chem. 64: pp. 1304-1307.
Jui-Hsien Huang, "Synthesis and structure characterization of 2-(dimethylaminomethyl)pyrrolate and 2,5-bis(dimethylaminomethyl)pyrrolate zirconium complexes." Journal of the Chinese Chemical Society, 2000, 47(6): pp. 1191-1195.
Alberto R. Dias, "Synthesis, characterisation, crystal structure, reactivity and bonding in titanium complexes containing 2,3,4,5-tetramethylpyrrolyl." Journal of the Chemical Society—Dalton Transactions(6), 1997, pp. 1055-1061.
R. Vann Bynum, "Pyrrolyl complexes of the early transition metals. 1. Synthesis and crystal structure of (η5-C5H5)2Ti(η 1-NC4H4)2." Inorg. Chem., 1980 19(8): pp. 2368-2374.
D.C. Bradley, "Metallo-organic compounds containing metal-nitrogen bonds. Part V. Dialkylamidopyrrolyl- and dialkylamido-2,5-dimethyl-pyrrolyltitanium compounds" J. Chem. Soc., A Field Full Journal Title:Journal of the Chemical Society [Section] A: Inorganic, Physical, Theoretical, 1968, (8): pp. 1967-1969.
Norbert Kuhn, "XVI. (2,5-C4tBu2RHN)MCl3 (M = Ti, Zr, Hf; R = H, SiMe3)—Azacyclopentadienyl-Komplexe der Gruppe 4-Metalle." Journal of Organometallic Chemistry, 1992, 440(3): pp. 289-296.
Joao L. Ferreira da Silva, "Effect of ancillary ligands in the hapticity of the pyrrolyl ligand in [Ti(pyrrolyl)(NMe2)xCl3-x] (x = 0, 1, 2, 3) complexes." Journal of Organometallic Chemistry, 2010, 695(10-11): pp. 1533-1540.
Joseph M. Tanski, "Synthesis and structures of zirconium-pyrrolyl complexes: Computational analysis of the factors that influence the coordination modes of pyrrolyl ligands." Organometallics, 2010, 21(4): pp. 587-589.
Douglas L. Swartz II, "Synthesis, Structure, and Hydroamination Kinetics of (2,2'-Diaryldipyrrolylmethane)- and Bis(2-arylpyrrolyl)titanium Complexes." Organometallics, 2006, 25(26): pp. 6125-6133.
Kate Black, "Investigation of new 2,5-dimethylpyrrolyl titanium alkylamide and alkoxide complexes as precursors for the liquid injection mocvd of TiO2." Chemical Vapor Deposition, 2010,16(1-3): pp. 93-99.
Alberto R. Dias, "Bonding Geometry of Pyrrolyl in Zirconium Complexes: Fluxionality between σ and π Coordination." Organometallics, 2003, 22(24): pp. 5114-5125.
Y. Li, "Group-4 η1-pyrrolyl complexes incorporating N,N-di(pyrrolyl-α-methyl)-N-methylamine." Inorganic Chemistry, 2002, 41(24): pp. 6298-6306.

* cited by examiner

*Primary Examiner* — Shawquia Young
(74) *Attorney, Agent, or Firm* — Rosaleen P. Morris-Oskanian

(57) ABSTRACT

Metal-containing complexes with general formula (1) $(R^1{}_nPyr)(R^2{}_nPyr)ML^1L^2$; or (2) $[(R^8XR^9)(R^1{}_nPyr)(R^2{}_nPyr)]ML^1L^2$ are disclosed; wherein M is a Group IV metal, Pyr is pyrrolyl ligand, n=1, 2 and 3, $L^1$ and $L^2$ are independently selected from alkoxide, amide or alkyl, $L^1$ and $L^2$ can be linked together, $R^1$ and $R^2$ can be same or different organic groups substituted at 2,3,4-positions of the pyrrole ring and are selected from the group consisting of linear and branched $C_{1-6}$ alkyls, $R^8$ and $R^9$ are independently selected from the linear or branched chain alkylene group having 2-6 carbon atoms, and X is $CH_2$ or oxygen. Methods of using the metal complexes as precursors to deposit metal or metal oxide films used for various devices in semi-conductor industries are also discussed.

18 Claims, 4 Drawing Sheets

GROUP IV METAL COMPLEXES FOR METAL-CONTAINING FILM DEPOSITION

CROSS REFERENCE TO RELATED APPLICATION

The present patent application claims the benefit of prior U.S. Provisional Patent Application Ser. No. 61/440,469 filed Feb. 8, 2011.

BACKGROUND OF THE INVENTION

The semiconductor industry is currently considering the use of thin metal or metal containing films for a variety of applications. Many organometallic complexes have been evaluated as potential precursors for the formation of these thin films. Relevant art to this field includes:

Black, K., A. C. Jones, J. Bacsa, P. R. Chalker, P. A. Marshall, H. O. Davies, P. N. Heys, P. O'Brien, M. Afzaal, J. Raftery and G. W. Critchlow, "Investigation of new 2,5-dimethylpyrrolyl titanium alkylamide and alkoxide complexes as precursors for the liquid injection MOCVD of $TiO_2$." Chemical Vapor Deposition 16(1-3): 93-99 (2010).

Bradley, D. C. and M. H. Gitlitz, "Metallo-organic compounds containing metal-nitrogen bonds. Part V. Dialkylamidopyrrolyl- and dialkylamido-2,5-dimethyl-pyrrolyltitanium compounds" J. Chem. Soc., A FIELD Full Journal Title: Journal of the Chemical Society [Section] A: Inorganic, Physical, Theoretical(8): 1967-9 (1968).

Bynum, R. V., W. E. Hunter, R. D. Rogers and J. L. Atwood, "Pyrrolyl complexes of the early transition metals. 1. Synthesis and crystal structure of $(\eta^5\text{-}C_5H_5)_2Ti(\eta^1\text{---}NC_4H_4)_2$" Inorg. Chem. 19(8): 2368-74 (1980).

Bynum, R. V., H.-M. Zhang, R. D. Rogers and J. L. Atwood, "Pyrrolyl complexes of the early transition metals. 3. Synthesis and crystal structure of $(\eta^5C_5H_5)_2Ti(\eta^1\text{---}NC_4H_2Me_2)_2$ and $(\eta^5C_5H_5)_2Zr(\eta^1\text{---}NC_4H_2Me_2)_2$" Can. J. Chem. 64: 1304. (1986).

WO09155507A and WO09155520A1 by Davies, H. O., P. N. Heys, A. Kingsley and R. Odedra.

Dias, A. R., A. P. Ferreira and L. F. Veiros, "Bonding Geometry of Pyrrolyl in Zirconium Complexes: Fluxionality between σ and π Coordination." Organometallics 22(24): 5114-5125 (2003).

Dias, A. R., A. M. Galvão, A. C. Galvão and M. S. Salema, "Synthesis, characterisation, crystal structure, reactivity and bonding in titanium complexes containing 2,3,4,5-tetramethylpyrrolyl." Journal of the Chemical Society—Dalton Transactions 1055-1061 (1997).

Ferreira da Silva, J. L. and A. C. Galvão, Ferreira, A. P., Galvão, A. M., Dias, A. R., Gomes, P. T., Salema, M. S., "Effect of ancillary ligands in the hapticity of the pyrrolyl ligand in $[Ti(pyrrolyl)(NMe_2)_xCl_{3-x}]$ (x=0, 1, 2, 3) complexes." Journal of Organometallic Chemistry 695(10-11): 1533-1540 (2010).

DE4120344A by Heinen, R. and T. Kruck.

WO2009086263 by Heys, P. N. and H. O. Davies.

Huang, J. H., P. C. Kuo, G. H. Lee and S. M. Peng, Synthesis and structure characterization of 2-(dimethylaminomethyl)pyrrolate and 2,5-bis(dimethylaminomethyl)pyrrolate zirconium complexes" Journal of the Chinese Chemical Society 47(6): 1191-1195 (2000).

Kuhn, N., S. Stubenrauch, R. Boese and D. Bläser, "XVI. $(2,5\text{-}C_4{}^tBu_2RH_2N)MCl_3$ (M=Ti, Zr, Hf; R=H, $SiMe_3$)—Azacyclopentadienyl-Komplexe der Gruppe 4-Metalle." Journal of Organometallic Chemistry 440(3): 289-296 (1992).

Li, Y., A. Turnas, J. T. Ciszewski and A. L. Odom, "Group-4 η1-pyrrolyl complexes incorporating N,N-di(pyrrolyl-α-methyl)-N-methylamine." Inorganic Chemistry 41(24): 6298-6306 (2002).

U.S. Pat. No. 7,332,618 by Meiere, S. H.

US20080081922A1 by Meiere, S. H., J. D. Peck, R. F. Spohn and D. M. Thompson.

U.S. Pat. No. 5,300,321A by Nakano, T. and T. Ohta.

Swartz II, D. L. and A. L. Odom in "Synthesis, Structure, and Hydroamination Kinetics of (2,2'-Diaryldipyrrolylmethane)- and Bis(2-arylpyrrolyl)titanium Complexes." Organometallics 25(26): 6125-6133 (2006).

Tanski, J. M. and G. Parkin, "Synthesis and structures of zirconium-pyrrolyl complexes: Computational analysis of the factors that influence the coordination modes of pyrrolyl ligands." Organometallics 21(4): 587-589 (2002).

A need still exists in the industry for developing new compounds and for exploring their potential as chemical vapor deposition (CVD) and atomic layer deposition(ALD) precursors for film depositions.

BRIEF SUMMARY OF THE INVENTION

This invention is directed to a novel family of Group IV metal complexes which can be potentially used as precursors to deposit metal or metal oxide films in semi-conductor industries.

One embodiment of this invention is directed to metal containing complexes with (1) a formula of $(R^1{}_n\text{Pyr})(R^2{}_n\text{Pyr})ML^1L^2$ having a structure A below:

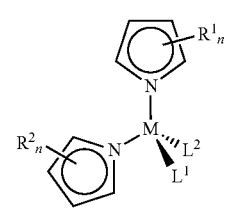

A wherein M is a Group IV metal selected from the group of titanium, zirconium, and hafnium, Pyr is pyrrolyl ligand, $R^1$ and $R^2$ can be same or different organic groups substituted at 2,3,4,5-positions of the pyrrole ring and selected from the group consisting of linear or branched $C_{1-6}$ alkyls, and $C_{3-10}$ alkyls containing oxygen or nitrogen atoms, preferably —$CH_2CH_2OMe$ and —$CH_2CH_2NMe_2$; n is 1, 2, 3 or 4, and one of each of $R^1$ and $R^2$ can be linked together via carbon, oxygen, or nitrogen atom; and $L^1$ and $L^2$ are independently selected from the group consisting of alkoxide, amide and alkyl, and can be linked together;

or (2) a formula of $[(R^8XR^9)(R^1{}_n\text{Pyr})(R^2{}_n\text{Pyr})]ML^1L^2$ having a structure B below:

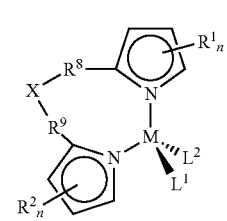

B wherein M is a Group IV metal selected from the group of titanium, zirconium, and hafnium, Pyr is pyrrolyl ligand, $R^1$ and $R^2$ can be same or different organic groups substituted at 2,3,4-positions of the pyrrole ring and selected from linear or branched $C_{1-6}$ alkyls, n=1, 2 and 3, $R^8$ and $R^9$ are independently selected from linear or branched chain alkylene group having 2-6 carbon atoms, and X is selected from the group consisting of $CH_2$ and oxygen, alkylamine, dialkyl silyl, and $L^1$ and $L^2$ are independently selected from the group consisting of alkoxide, amide and alkyl, and can be linked together.

Another embodiment of this invention is directed to the methods for making the metal containing complexes represented above.

Yet, another embodiment of this invention is directed to the methods for depositing metal containing films by employing the metal containing complexes represented above.

DETAILED DESCRIPTION OF THE INVENTION

Figure 1:
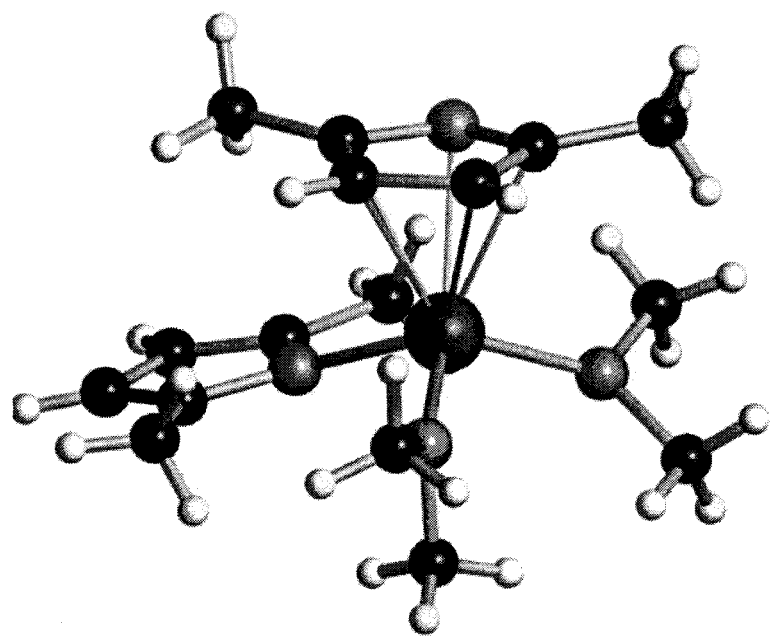
FIG. 1. Crystal Structure of metal complex bis(2,5-dimethyl-pyrrolyl)bis(dimethylamino)zirconium.

With each generation of metal oxide semiconductor (MOS) integrated circuit (IC), the device dimensions have been continuously scaled down to provide for high-density and high-performance, such as high speed and low power consumption requirements. Unfortunately, field effect semiconductor devices produce an output signal that is proportional to the width of the channel, such that scaling reduces their output. This effect has generally been compensated for by decreasing the thickness of gate dielectric, thus bring the gate in closer proximity to the channel and enhancing the field effect, which thereby increases the drive current. Therefore, it has become increasingly important to provide extremely thin reliable and low-defect gate dielectrics for improving device performance.

The invention relates to the Group IV metal complexes. Also described herein is a method for making a Group IV metal-containing oxide film, metal-containing nitride film, metal-containing oxynitride film, metal-containing silicate film, multi-component metal oxide film, and any combination or laminate thereof, which may be used, for example, in fabricating semiconductor devices. In one embodiment, the method disclosed herein provides a Group IV metal or multi-component metal oxide film that has a dielectric constant substantially higher than that of either conventional thermal silicon oxide, silicon nitride, or zirconium/hafnium oxide dielectric.

In addition to minimizing side reactions with the substrate that the Group IV precursor is deposited upon, it is also desirable that the Group IV precursor is thermally stable, and preferably in liquid form. Group IV metal-containing films are typically deposited using a vapor deposition (e.g., chemical vapor deposition and/or atomic layer deposition) process. It is desirable that these precursors are thermally stable during vapor delivery in order to avoid premature decomposition of the precursor, before it reaches the vapor deposition chamber during processing.

One embodiment is directed to metal containing complexes with (1) a formula of $(R^1{}_n PYr)(R^2{}_n Pyr)ML^1L^2$ having a structure A below:

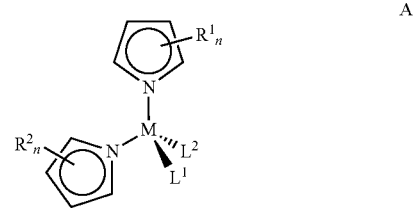

A where M is a Group IV metal selected from the group of titanium, zirconium or hafnium, Pyr is pyrrolyl ligand, $R^1$ and $R^2$ can be same or different organic groups substituted at 2,3,4,5-positions of the pyrrole ring and selected from the group consisting of linear or branched $C_{1-6}$ alkyls, and $C_{3-10}$ alkyls containing oxygen or nitrogen atoms, preferably —$CH_2CH_2OMe$ and —$CH_2CH_2NMe_2$; n is 1, 2, 3 or 4, and one of each of $R^1$ and $R^2$ can be linked together via carbon, oxygen, or nitrogen atom; and $L^1$, $L^2$ are independently selected from the group consisting of alkoxide, amide and alkyl, and can be linked together;

or (2) a formula of $[(R^8XR^9)(R^1{}_n Pyr)(R^2{}_n Pyr)]ML^1L^2$ having a structure B below:

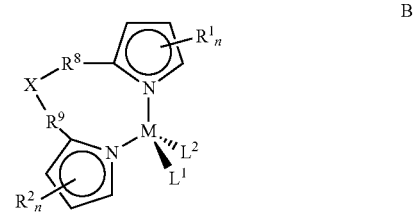

B where $R^1$ and $R^2$ can be same or different organic groups substituted at 2,3,4-positions of the pyrrole ring and selected from the group consisting of linear or branched $C_{1-6}$ alkyls, n=1, 2 and 3, W and $R^9$ are independently selected from the group consisting of linear or branched chain alkylene group having 2-6 carbon atoms, and X is selected from the group consisting of $CH_2$, oxygen, alkylamino, dialkyl silyl, and $L^1$, $L^2$ are independently selected from the group consisting of alkoxide, amide and alkyl, and can be linked together.

Example 1 of the embodiment is represented by the formula $(R^1{}_n Pyr)(R^2{}_n Pyr)M(NR^3R^4)_2$ having a structure below:

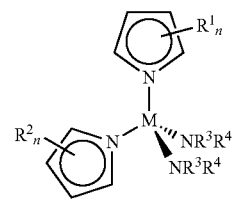

where $R^3$ and $R^4$ are independently selected from methyl and ethyl.

Exemplary complexes include but are not limited to: bis(2,5-dimethyl-pyrrolyl)bis(dimethylamino)'titanium, bis(2,5-dimethyl-pyrrolyl)bis(dimethylamino)zirconium, bis(2,5-dimethyl-pyrrolyl)bis(dimethylamino)hafnium, bis(2,5-dimethyl-pyrrolyl)bis(ethylmethylamino)titanium, bis(2,5-dimethyl-pyrrolyl)bis(ethylmethylamino)zirconium, bis(2,5-dimethyl-pyrrolyl)bis(ethylmethylamino)hafnium, bis(2,5-dimethyl-pyrrolyl)bis(diethylamino)titanium, bis(2,5-dimethyl-pyrrolyl)bis(diethylamino)zirconium, bis(2,5-dimethyl-pyrrolyl)bis(diethylamino)hafnium, bis(2,3,4,5-tetramethyl-pyrrolyl)bis(dimethylamino)titanium, bis(2,3,4,5-tetramethyl-pyrrolyl)bis(dimethylamino)zirconium, bis(2,3,4,5-tetramethyl-pyrrolyl)bis(dimethylamino)hafnium, bis(2,5-di-tert-butyl-pyrrolyl)bis(dimethylamino)titanium, bis(2,5-di-tert-butyl-pyrrolyl)bis(dimethylamino)zirconium, bis(2,5-di-tert-butyl-pyrrolyl)bis(dimethylamino)hafnium, bis(2,5-di-tert-butyl-pyrrolyl)bis(dimethylamino)titanium, bis(2,5-di-tert-butyl-pyrrolyl)bis(dimethylamino)zirconium, bis(2,5-di-tert-butyl-pyrrolyl)bis(dimethylamino)hafnium, (2,5-dimethyl-pyrrolyl)(2,5-di-tert-butyl-pyrrolyl)bis(dimethylamino)titanium, (2,5-dimethyl-pyrrolyl)(2,5-di-tert-butyl-pyrrolyl)bis(dimethylamino)zirconium, and (2,5-dimethyl-pyrrolyl)(2,5-di-tert-butyl-pyrrolyl)bis(dimethylamino)hafnium.

Example 2 of the embodiment is represented by the formula $(R^1_n Pyr)(R^2_n Pyr)M(R^3 NXNR^4)$, having a structure below:

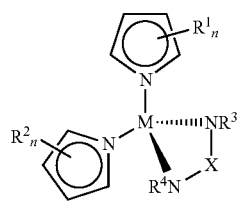

where $R^3$ and $R^4$ are independently selected from methyl and ethyl, and X is a linear or branched alkylene group having 2-6 carbon atoms.

Example 3 of the embodiment is represented by the formula $(R^1_n Pyr)(R^2_n Pyr)M(OR^5)(OR^6)$ having a structure below:

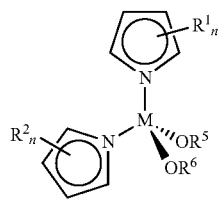

wherein $R^5$ and $R^6$ are independently selected from the group consisting of linear or branched $C_{1-6}$ alkyls.

Example 4 of the embodiment is represented by the formula $(R^1_n Pyr)(R^2_n Pyr)M(R^6 R^7 OR^5 OR^8 R^9)$ having a structure below:

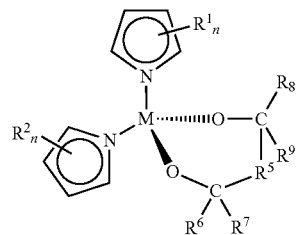

wherein $R^5$ is selected from the group consisting of linear or branched $C_{1-6}$ alkyls and $R^{6-9}$ are independently selected from the group consisting of hydrogen, linear or branched $C_{1-6}$ alkyls.

Exemplary complexes include but are not limited to: bis(2,5-dimethyl-pyrrolyl)(2-methyl-2,4-pentanediolate)titanium, bis(2,5-dimethyl-pyrrolyl)(2-methyl-2,4-pentanediolate)zirconium, bis(2,5-dimethyl-pyrrolyl)(2-methyl-2,4-pentanediolate)hafnium, bis(2,3,4,5-tetramethyl-pyrrolyl)(2-methyl-2,4-pentanediolate)titanium, bis(2,3,4,5-tetramethyl-pyrrolyl)(2-methyl-2,4-pentanediolate)zirconium, bis(2,3,4,5-tetramethyl-pyrrolyl)(2-methyl-2,4-pentanediolate)hafnium, bis(2,5-di-tert-butyl-pyrrolyl)(2-methyl-2,4-pentanediolate)titanium, bis(2,5-di-tert-butyl-pyrrolyl)(2-methyl-2,4-pentanediolate)zirconium, and bis(2,5-di-tert-butyl-pyrrolyl)(2-methyl-2,4-pentanediolate)hafnium.

Example 5 of the embodiment is represented by the formula $(R^1_n Pyr)(R^2_n Pyr)M(OR^{10})(R^{11})$ having a structure below:

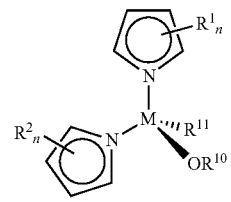

where $R^{10}$ and $R^{11}$ are independently selected from the group consisting of linear or branched $C_{1-6}$ alkyls.

In all structure disclosed above, the pyrrolyl ligands can be coordinated to the metal center in either $\eta^1$ or $\eta^5$ coordination mode.

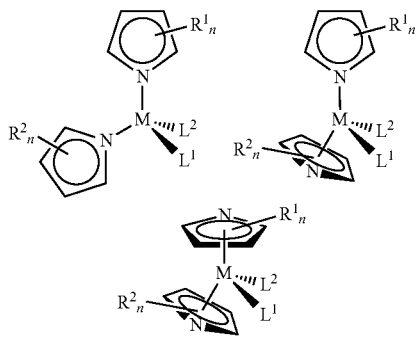

Preferentially at least one pyrrolyl ligand is coordinated to the metal center in $\eta^5$ coordination mode. Without being bound by any theory it is believed that $\eta^5$ coordination of at least one pyrrolyl mode to the metal center provides additional stabilization of the metal complex.

The term "linear or branched alkyl" throughout the description denotes a hydrocarbon group having from 1 to 6 carbon atoms, preferably from 1 to 3 carbon atoms. Exemplary alkyl groups include, but are not limited to, methyl, ethyl, n-propyl, iso-propyl, n-butyl, iso-butyl, sec-butyl, tert-butyl, n-pentyl, iso-pentyl, tert-pentyl, hexyl.

An example of such complex is bis(2,5-dimethyl-pyrrolyl) bis(dimethylamino)zirconium.

The metal containing complexes disclosed above are used as precurors for depositing Group IV metal-containing films, such as but not limited to, oxide film, metal-containing nitride film, metal-containing oxynitride film, metal-containing silicate film, multi-component metal oxide film, and any combination or laminate thereof. More specifically the films include titanium dioxide, doped titanium dioxide, strontium titanate and barium strontium titanate, titanium doped lanthanide oxide, titanium doped zirconium oxide, titanium doped hafnium oxide films. Those films are used, for example, as a gate dielectric or capacitor dielectric film in a semiconductor device. The Group IV metal or multi-component metal oxide film will have a dielectric constant substantially higher than that of either conventional thermal silicon oxide, silicon nitride, or zirconium/hafnium oxide dielectric.

The deposition method disclosed herein include but not limited to, atomic layer deposition (ALD) or cyclic chemical vapor deposition (CCVD) processes, preferably an ALD process. Examples of other suitable deposition processes for the method disclosed herein include, but are not limited to, cyclic chemical vapor deposition (CCVD), MOCVD metal organic chemical vapor deposition (MOCVD), thermal chemical vapor deposition, plasma enhanced chemical vapor deposition (PECVD), photon assisted chemical vapor deposition (PACVD), plasma-photon assisted chemical vapor deposition (PPECVD), cryogenic chemical vapor deposition, chemical assisted vapor deposition, and hot-filament chemical vapor deposition. In certain embodiments, the metal containing films are deposited via thermal ALD or plasma enhanced cyclic ALD (PEALD) process.

In the deposition process, the deposition temperature may be relatively lower, preferably a range from 200° C. to 500° C., and may allow for a wider process window to control the specifications of film properties required in end-use applications. Exemplary deposition temperatures for the ALD or CCVD deposition include ranges having any one or more of the following endpoints: 200, 225, 250, 275, 300, 325, 350, 375, and/or 400° C.

In certain embodiments, other metal-containing precursors can be used in addition to the Group IV metal-containing precursors described herein. Metals commonly used in semiconductor fabrication, include those that can be used as the metal component such as: titanium, tantalum, tungsten, hafnium, zirconium, cerium, zinc, thorium, bismuth, lanthanum, strontium, barium, lead, and combinations thereof.

Examples of other metal-containing precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino) hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino) tantalum (TBTDET), tert-butylimino tri(dimethylamino) tantalum (TBTDMT), tert-butylimino tri(ethylmethylamino) tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, bis(2,2,6,6-tetramethyl-3,5-heptanedionato)strontium, bis(2,2,6,6-tetramethyl-3,5-heptanedionato)barium, tris(2,2,6,6-tetramethyl-3,5-heptanedionato)lanthanides; $M(R_m C_{5-m-n} H_n)_2$ wherein M=Sr or Ba, n is a integer from 1 to 4, n+m=5; $M(R_m C_{5-m-n} H_n)_3$ wherein M=lanthanide elements such as La, Pr, Nd, Gd, Er, Yb, Lu, n is a integer from 1 to 4, n+m=5, and combinations thereof.

The cyclic deposition processes such as CCVD, ALD, or PEALD may be employed, wherein a Group IV metal-containing precursor or its solution and an oxygen source such as, for example, ozone, oxygen plasma or water plasma are employed.

The deposition conditions further include but not limited to the following. The gas lines connecting from the precursor canisters to the reaction chamber are heated to one or more temperatures ranging from about 100° C. to about 200° C. depending upon the process requirements, and the container of the Group IV metal-containing precursor is kept at one or more temperatures ranging from about 100° C. to about 190° C. for dispensing, wherein the solution comprising the Group IV metal-containing precursor is injected into a vaporizer kept at one or more temperatures ranging from about 150° C. to about 200° C. for direct liquid injection. A flow of 100-2000 sccm of inert gas such as argon or nitrogen may be employed as a carrier gas to help deliver the vapor of the Group IV metal-containing precursor to the reaction chamber during the precursor pulsing. The reaction chamber process pressure is in the range of 0.1 to 10 Torr.

In a typical ALD or CCVD process, the substrate, such as silicon oxide or metal nitride, is heated on a heater stage in a reaction chamber that is exposed to the Group IV metal-containing precursor initially to allow the complex to chemically adsorb onto the surface of the substrate. An inert gas, such as argon, purges away unadsorbed excess complex from the process chamber. After sufficient Ar purging, an oxygen source is introduced into reaction chamber to react with the absorbed surface followed by another inert gas purge to remove reaction by-products from the chamber. The process cycle can be repeated to achieve the desired film thickness.

In liquid delivery formulations, the precursors described herein may be delivered in neat liquid form, or alternatively, may be employed in solvent formulations or compositions comprising same. Thus, in certain embodiments the precursor formulations may include solvent component(s) of suitable character, as may be desirable and advantageous in a given end use application to form a film on a substrate.

The solvent employed in solubilizing the precursor for use in a deposition process may comprise any compatible solvent or their mixture, including; aliphatic hydrocarbons (e.g., pentane, hexane, heptane, octane, decane, dodecane, ethylcyclohexane, propylcyclohexane), aromatic hydrocarbons (e.g., benzene, toluene, ethylbenzene, xylene, mesitylene, ethyl toluene and other alkyl substituted aromatic solvents), ethers, esters, nitriles, alcohols, amines (e.g., triethylamine, tert-butylamine), imines and carbodiimides (e.g., N,N'-diisopropylcarbodiimide), ketones, aldehydes, amidines, guanadines, isoureas, and the like.

Further examples of suitable solvents are selected from the group consisting of glyme solvents having from 1 to 6 oxygen atoms (e.g. dimethoxyethane, 1,2-diethoxyethane, diglyme and triglyme); organic ethers selected from the group consisting of propylene glycol groups (e.g. dipropylene glycol dimethyl ether); $C_2$-$C_{12}$ alkanols; organic ethers selected from the group consisting of dialkyl ethers comprising $C_1$-$C_6$ alkyl moieties, $C_4$-$C_8$ cyclic ethers (e.g. tetrahydrofuran and dioxane); $C_{12}$-$C_{60}$ crown $O_4$-$O_{20}$ ethers wherein the prefixed $C_1$ range is the number i of carbon atoms in the ether compound and the suffixed $O_1$ range is the number i of oxygen atoms in the ether compound; $C_6$-$C_{12}$ aliphatic hydrocarbons; $C_6$-$C_{18}$ aromatic hydrocarbons; organic esters; organic amines, polyamines, aminoethers and organic amides.

Another class of solvents that offers advantages is the organic amide class of the form RCONR'R" wherein R and R' are alkyl having from 1-10 carbon atoms and they can be connected to form a cyclic group $(CH_2)_n$, wherein n is from 4-6, preferably 5, and R" is selected from alkyl having from 1 to 4 carbon atoms and cycloalkyl. N-methyl- or N-ethyl- or N-cyclohexyl-2-pyrrolidinones, N,N-Diethylacetamide, and N,N-Diethylformamide are examples.

The utility of specific solvent compositions for particular precursors may be readily empirically determined, to select an appropriate single component or multiple component solvent medium for the liquid delivery vaporization and transport of the specific copper precursor that is employed.

In some embodiments, a direct liquid delivery method can be employed by dissolving the Group IV metal-containing precursors in a suitable solvent or a solvent mixture to prepare a solution with a molar concentration from 0.01 to 2 M, depending the solvent or mixed-solvents employed. The solvent employed herein may comprise any compatible solvents or their mixture including, but not limited to, aliphatic hydrocarbons, aromatic hydrocarbons, linear or cyclic ethers, esters, nitriles, alcohols, amines, polyamines, aminoethers and organic amides, preferably a solvent with a high boiling point, such as octane, ethylcyclohexane, decane, dodecane, xylene, mesitylene and dipropylene glycol dimethyl ether.

In one particular embodiment, the resultant metal oxide films can be exposed to a post-deposition treatment, such as a thermal or plasma treatment to densify the film at temperature below 600° C.

The deposition method described herein may be used to deposit a metal-containing film on at least a portion of a substrate. Examples of suitable substrates include, but are not limited to, semiconductor materials, such as strontium titanate, barium strontium titanate, yttrium oxide doped with titanium, lanthanum oxide doped with titanium, and other lanthanide oxides doped with titanium.

The following examples illustrate the method for preparing a Group IV metal-containing precursor described herein are not intended to limit it in any way.

EXAMPLES

Example 1

Synthesis of bis(2,5-dimethyl-pyrrolyl)bis(dimethylamino)zirconium

In a $N_2$-purged glove box a 250 mL, 3-neck round bottom flask equipped with a magnetic stir bar, thermocouple, and shortpath distillation column was charged with the 25.50 g (95.3 mmol) of tetrakis(dimethylamino)zirconium and 50 mL of anhydrous toluene. 19.04 g (200.2 mmol) of 2,5-dimethylpyrrole (Aldrich, pre-dried over 3 A molecular sieves for 24 hours) were dissolved in 50 mL of anhydrous toluene and the solution was added dropwise to the toluene solution of tetrakis(dimethylamino)zirconium at room temperature during ~5 min. The temperature of the reaction mixture increased to 48° C. during the addition. The reaction was agitated for 1 hour and heated to 110° C. under nitrogen flow. Most of toluene was distilled out under ambient pressure along with the reaction by-product, dimethylamine. Remaining toluene and 2,5-dimethylpyrrole were removed under vacuum (100 mtorr) at 80° C. 35.99 g of dark crystalline product were isolated with ~100% crude yield. The product was purified by sublimation to isolate 24.8 g of bis(2,5-dimethyl-pyrrolyl)bis(dimethylamino)zirconium, light yellow solid, mp ~87° C., 70.9% purified yield. $^1$H-NMR (500 MHz, $C_6D_6$) δ(ppm): 6.05 (s, 4H), 2.82 (q, 12H), 2.10 (t, 12H).

The crystal structure of bis(2,5-dimethyl-pyrrolyl)bis(dimethylamino)zirconium has been shown in FIG. 1.

Figure 2:
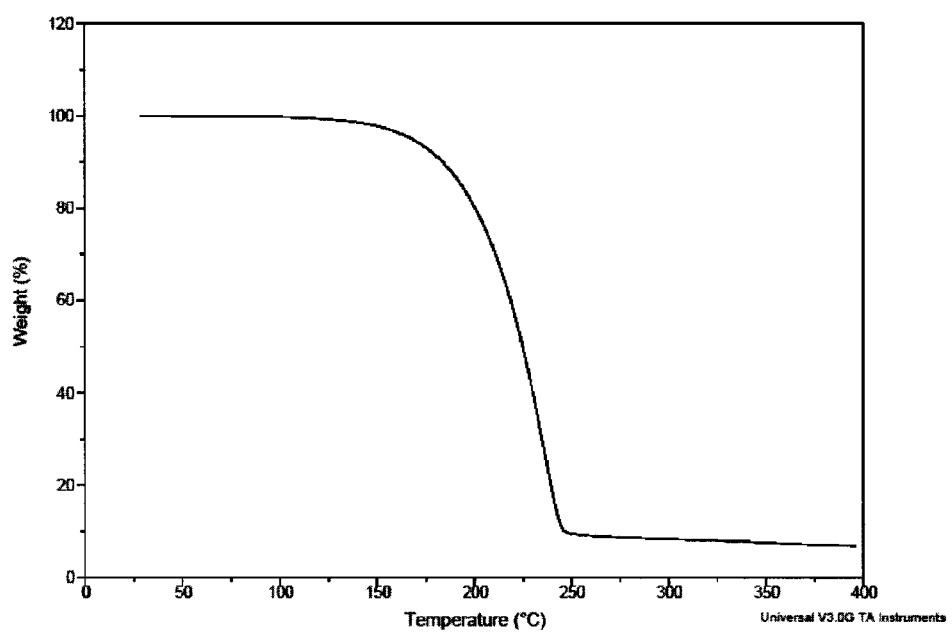
FIG. 2. Thermal gravimetric analysis (TGA) of bis(2,5-dimethyl-pyrrolyl)bis(dimethylamino)zirconium.

Thermal gravimetric analysis (TGA) of bis(2,5-dimethyl-pyrrolyl)bis(dimethylamino)zirconium has been shown in FIG. 2. The TGA result indicated that bis(2,5-dimethyl-pyrrolyl)bis(dimethylamino)zirconium is volatile and has low involatile residue.

Figure 3:
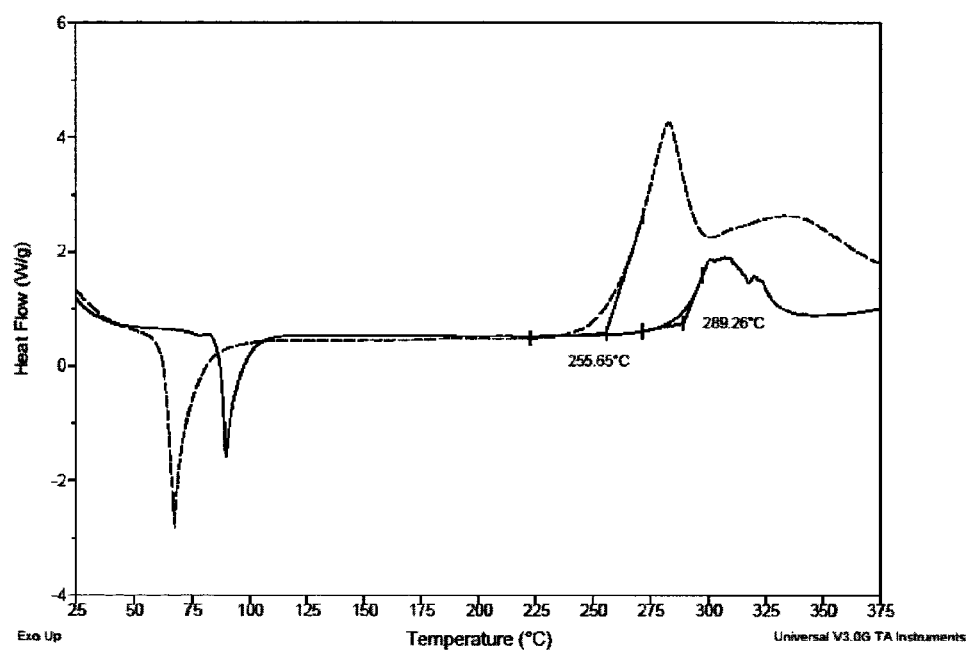
FIG. 3. The scanning calorimetry of bis(2,5-dimethyl-pyrrolyl)bis(dimethylamino)zirconium (solid line) and tetrakis (dimethylamino)zirconium (dashed line)

FIG. 3 showed the comparison of differential scanning calorimetry of bis(2,5-dimethyl-pyrrolyl)bis(dimethylamino)zirconium, the precursor of this invention (solid line), and tetrakis(dimethylamino)zirconium, the precursor of prior art(dashed line). Decomposition of both precursors has been characterized by an exothermic effect. However, extrapolated onset of thermal decomposition of bis(2,5-dimethyl-pyrrolyl) bis(dimethylamino)zirconium (289° C.) was >30° C. higher compare to extrapolated onset of thermal decomposition of tetrakis(dimethylamino)zirconium (256° C.). The result suggested that bis(2,5-dimethyl-pyrrolyl)bis(dimethylamino) zirconium has better thermal stability compare to tetrakis (dimethylamino)zirconium.

Example 2

Synthesis of bis(2,5-dimethyl-pyrrolyl)bis(ethylmethylamino)zirconium

In a $N_2$-purged glove box a 100 mL, 3-neck round bottom flask equipped with a magnetic stir bar, thermocouple, and shortpath distillation column was charged with the 3.0 g (9.3 mmol) of tetrakis(ethylmethylamino)zirconium and 20 mL of anhydrous toluene. 1.852 g (19.5 mmol) of 2,5-dimethylpyrrole (Aldrich, pre-dried over 3 A molecular sieves for 24 hours) were dissolved in 20 mL of anhydrous toluene and the solution was added to the toluene solution of tetrakis(ethylmethylamino)zirconium at room temperature during ~5 min. The reaction was agitated for 1 hour and heated to 110° C. under nitrogen flow. Most of toluene was distilled out under ambient pressure along with the reaction by-product, ethylmethylamine. Remaining toluene and 2,5-dimethylpyrrole were removed under vacuum (100 mtorr) at 80° C. Crude product was purified by sublimation to isolate 2.51 g of bis (2,5-dimethyl-pyrrolyl)bis(ethylmethylamino)zirconium, light yellow solid, mp ~95° C., 68% purified yield. $^1$H-NMR (500 MHz, $C_6D_5CD_3$) δ (ppm): 6.08 (s, 4H), 3.12 (q, 4H), 2.90 (s, 6 H), 2.12 (s, 12 H), 0.88 (t, 6H).

Example 3

Figure 4:
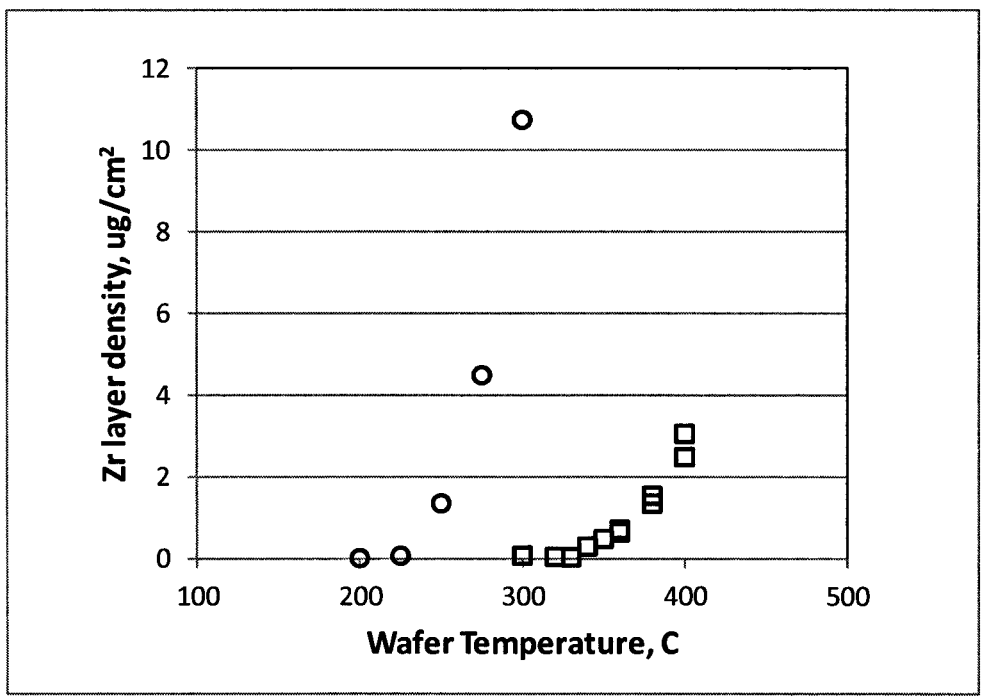
FIG. 4. The dependence of Zr layer density in the thin films deposited by exposing silicon wafer to 100 cycles of zirconium precursor pulse/Ar purge. Circle-tetrakis(ethylmethylamino)zirconium, square-bis(2,5-dimethyl-pyrrolyl)bis (dimethylamino)zirconium.

The comparison of the onset of thermal decomposition on silicon wafer surface of tetrakis(ethylmethylamino)zirconium and bis(2,5-dimethylpyrrolyl)bis (dimethylamino)zirconium In this experiment vapors of tetrakis(ethylmethylamino) zirconium and bis(2,5-dimethylpyrrolyl)bis(dimethylamino)

zirconium were delivered to the deposition chamber in a pulsed mode separated by argon purge. Total number of precursor/Ar purgecycles was 100. No oxidant was used in this experiment in order to only compare thermal stability of two precursors in the absence of the oxidant. Wafer temperature was varied from 200-400° C. After the experiment Zr layer density on the surface was measured by X-Ray fluorescence analysis and is shown in FIG. 4. Thermal decomposition of bis(2,5-dimethylpyrrolyl)bis(dimethylamino)zirconium on the wafer surface occurred at significantly higher temperature (>320° C.) compare to thermal decomposition of the known in the art precursor-terakis(ethylmethylamino)zirconium (>240° C.). Higher thermal stability of bis(2,5-dimethylpyrrolyl)bis(dimethylamino)zirconium suggests that this precursor will have an extended thermal window in deposition of zirconium oxide by ALD process compare to the known in the art precursor-terakis(ethylmethylamino)zirconium.

Example 4

Atomic Layer Deposition of Zirconium Oxide

Process of depositing zirconium oxide films from bis(2,5-dimethypyrrolyl)bis(dimethylamino)zirconium by atomic layer deposition method include the following steps:
1. Introduction of zirconium precursor into the deposition chamber and chemisorption of zirconium precursor on the heated substrate;
2. Ar purge: purging away any unreacted Zr precursor with Ar;
3. Ozone pulse: introducing ozone into the deposition chamber to react with sorbed Zr precursor on the heated substrate; and,
4. Ar purge: purging away any unreacted ozone and by-products with Ar.

The other conditions for atomic layer deposition of zirconium oxide include: deposition temperature range is 250-350° C., precursor delivery mode: bubbling or direct liquid injection, and deposition chamber pressure: 1-2 Torr.

The invention claimed is:
1. A metal containing complex with
(1) a formula of $(R^1{}_n Pyr)(R^2{}_n Pyr)ML^1L^2$ having a structure A below:

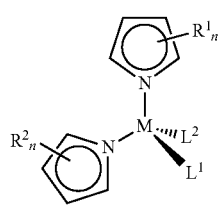

A wherein M is a Group IV metal selected from the group of titanium, zirconium and hafnium, Pyr is pyrrolyl ligand, $R^1$ and $R^2$ can be same or different organic groups substituted at 2,3,4,5-positions of the pyrrole ring and selected from the group consisting of linear or branched $C_{1-6}$ alkyls, and $C_{3-10}$ alkyls containing oxygen or nitrogen atoms; n is 1, 2, 3 or 4, and one of each of $R^1$ and $R^2$ can be linked together via carbon, oxygen, or nitrogen atom; and $L^1$ and $L^2$ are independently selected from the group consisting of alkoxide, amino and $C_2$-$C_6$ alkyl, and can be linked together;

or
(2) a formula of $[(R^8 XR^9)(R^1{}_n Pyr)(R^2{}_n Pyr)]ML^1L^2$ having a structure B below:

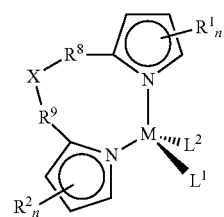

B wherein M is a Group IV metal selected from the group of titanium, zirconium and hafnium, Pyr is pyrrolyl ligand, $R^1$ and $R^2$ can be same or different organic groups substituted at 2,3,4-positions of the pyrrole ring and selected from linear or branched $C_{1-6}$ alkyls, n =1, 2 and 3, $R^8$ and $R^9$ are independently selected from linear or branched chain alkylene group having 2-6 carbon atoms, and X is selected from the group consisting of $CH_2$ and oxygen, alkylamino, dialkyl silyl, and $L^1$ and $L^2$ are independently selected from the group consisting of alkoxide, amide and alkyl, and can be linked together.

2. The metal containing complex of claim 1, wherein at least one pyrrolyl ligand is coordinated to the metal center in $\eta^5$ coordination mode.

3. The metal containing complex of claim 1 represented by the formula of $(R^1{}_n Pyr)(R^2{}_n Pyr)M(NR^3R^4)_2$ having a structure below:

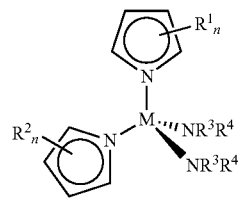

where $R^3$ and $R^4$ are independently selected from the group consisting of methyl and ethyl.

4. The metal containing complex of claim 3, is selected from the group consisting of bis(2,5-dimethyl-pyrrolyl)bis(dimethylamino)titanium, bis(2,5-dimethyl-pyrrolyl)bis(dimethylamino)zirconium, bis(2,5-dimethyl-pyrrolyl)bis(dimethylamino)hafnium, bis(2,5-dimethyl-pyrrolyl)bis(ethylmethylamino)titanium, bis(2,5-dimethyl-pyrrolyl)bis(ethylmethylamino)zirconium, bis(2,5-dimethyl-pyrrolyl)bis(ethylmethylamino)hafnium, bis(2,5-dimethyl-pyrrolyl)bis(diethylamino)titanium, bis(2,5-dimethyl-pyrrolyl)bis(diethylamino)zirconium, bis(2,5-dimethyl-pyrrolyl)bis(diethylamino)hafnium, bis(2,3,4,5-tetramethyl-pyrrolyl)bis(dimethylamino)titanium, bis(2,3,4,5-tetramethyl-pyrrolyl)bis(dimethylamino)zirconium, bis(2,3,4,5-tetramethyl-pyrrolyl)bis(dimethylamino)hafnium, bis(2,5-di-tert-butyl-pyrrolyl)bis(dimethylamino)titanium, bis(2,5-di-tert-butyl-pyrrolyl)bis(dimethylamino)zirconium, bis(2,5-di-tert-butyl-pyrrolyl)bis(dimethylamino)hafnium, bis(2,5-di-tert-butyl-pyrrolyl)bis(dimethylamino)titanium, bis(2,5-di-tert-butyl-pyrrolyl)bis(dimethylamino)zirconium, bis(2,5-di-tert-butyl-pyrrolyl)bis(dimethylamino)hafnium, (2,5-dimethyl-pyrrolyl)(2,5-di-tert-butyl-pyrrolyl)bis(dimethylamino)titanium, (2,5-dimethyl-pyrrolyl)(2,5-di-tert-butyl-pyrrolyl)bis(dimethylamino)zirconium, and (2,5-dimethyl-pyrrolyl)(2,5-di-tert-butyl-pyrrolyl)bis(dimethylamino)hafnium.

5. The metal containing complex of claim 1 represented by the formula of $(R^1{}_n Pyr)(R^2{}_n Pyr)M(NR^3 X NR^4)$, having a structure below:

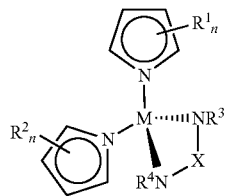

wherein $R^3$ and $R^4$ are independently selected from the group consisting methyl and ethyl, and X is a linear or branched chain alkylene group having 2-6 carbon atoms.

6. The metal containing complex of claim 1 represented by the formula of $(R^1{}_n Pyr)(R^2{}_n Pyr)M(OR^5)(OR^6)$ having a structure below:

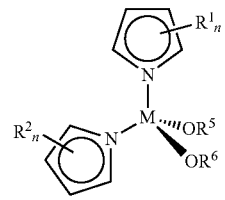

wherein $R^5$ and $R^6$ are independently selected from the group consisting of linear and branched $C_{1-6}$ alkyls.

7. The metal containing complex of claim 1 represented by the formula of $(R^1{}_n Pyr)(R^2{}_n Pyr)M(R^6 R^7 OR^5 OR^8 R^9)$ having a structure below:

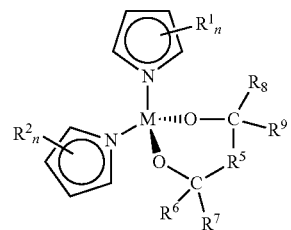

wherein $R^5$ is selected from the group consisting of linear or branched $C_{1-6}$ alkyls and $R^{6-9}$ are independently selected from the group consisting of hydrogen, linear or branched $C_{1-6}$ alkyls.

8. The metal containing complex of claim 7 is selected from the group consisting of bis(2,5-dimethyl-pyrrolyl)(2-methyl-2,4-pentanediolate)titanium, bis(2,5-dimethyl-pyrrolyl)(2-methyl-2,4-pentanediolate)zirconium, bis(2,5-dimethyl-pyrrolyl)(2-methyl-2,4-pentanediolate)hafnium, bis(2,3,4,5-tetramethyl-pyrrolyl)(2-methyl-2,4-pentanediolate)titanium, bis(2,3,4,5-tetramethyl-pyrrolyl)(2-methyl-2,4-pentanediolate)zirconium, bis(2,3,4,5-tetramethyl-pyrrolyl)(2-methyl-2,4-pentanediolate)hafnium, bis(2,5-di-tert-butyl-pyrrolyl)(2-methyl-2,4-pentanediolate)titanium, bis(2,5-di-tert-butyl-pyrrolyl)(2-methyl-2,4-pentanediolate)zirconium, and bis(2,5-di-tert-butyl-pyrrolyl)(2-methyl-2,4-pentanediolate)hafnium.

9. The metal containing complex of claim 1 represented by the formula $(R^1{}_n Pyr)(R^2{}_n Pyr)M(OR^{10})(R^{11})$ having a structure below:

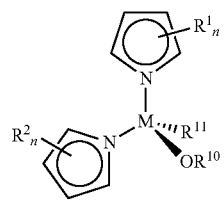

where $R^{10}$ and $R^{11}$ are independently selected from the group consisting of linear or branched $C_{1-6}$ alkyls.

10. A method for producing a film by depositing a metal containing complex with
(1) a formula of $(R^1{}_n Pyr)(R^2{}_n Pyr)ML^1 L^2$ having a structure A below:

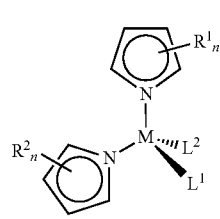

wherein M is a Group IV metal selected from the group of titanium, zirconium and hafnium, Pyr is pyrrolyl ligand, $R^1$ and $R^2$ can be same or different organic groups substituted at 2,3,4,5-positions of the pyrrole ring and selected from the group consisting of linear or branched $C_{1-6}$ alkyls, and $C_{3-10}$ alkyls containing oxygen or nitrogen atoms; n is 1, 2, 3 or 4, and one of each of $R^1$ and $R^2$ can be linked together via carbon, oxygen, or nitrogen atom; and $L^1$ and $L^2$ are independently selected from the group consisting of alkoxide, amino and $C_2$-$C_6$ alkyl, and can be linked together; or
(2) a formula of $((R^8 X R^9)(R^1{}_n Pyr)(R^2{}_n Pyr))ML^1 L^2$ having a structure B below:

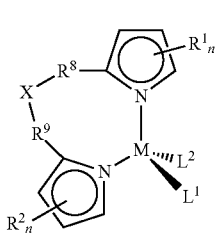

wherein M is a Group IV metal selected from the group of titanium, zirconium and hafnium, Pyr is pyrrolyl ligand, $R^1$ and $R^2$ can be same or different organic groups substituted at 2,3,4-positions of the pyrrole ring and selected from linear or branched $C_{1-6}$ alkyls, n =1, 2 and 3, $R^8$ and $R^9$ are independently selected from linear or branched chain alkylene group having 2-6 carbon atoms, and X is selected from the group consisting of $CH_2$ and oxygen, alkylamino, dialkyl silyl, and $L^1$ and $L^2$ are independently selected from the group consisting of alkoxide, amide and alkyl, and can be linked together.

11. The method of claim 10, wherein the depositing is selected from the group consisting of a chemical vapor deposition (CVD), cyclic chemical vapor deposition (CCVD), plasma enhanced cyclic chemical vapor deposition, an atomic layer deposition (ALD), and plasma enhanced atomic layer deposition.

12. A film by depositing a precursor comprising at least one metal containing complex with (1) a formula of $(R^1{}_n Pyr)(R^2{}_n Pyr)ML^1 L^2$ having a structure A below:

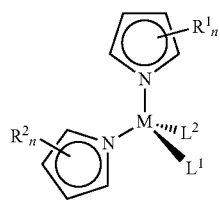

A wherein M is a Group IV metal selected from the group of titanium, zirconium and hafnium, Pyr is pyrrolyl ligand, $R^1$ and $R^2$ can be same or different organic groups substituted at 2,3,4,5-positions of the pyrrole ring and selected from the group consisting of linear or branched $C_{1-6}$ alkyls, and $C_{3-10}$ alkyls containing oxygen or nitrogen atoms; n is 1, 2, 3 or 4, and one of each of $R^1$ and $R^2$ can be linked together via carbon, oxygen, or nitrogen atom; and $L^1$ and $L^2$ are independently selected from the group consisting of alkoxide, amino and $C_2$-$C_6$ alkyl, and can be linked together; or (2) a formula of $((R^8 X R^9)(R^1{}_n Pyr)(R^2{}_n Pyr))ML^1 L^2$ having a structure B below:

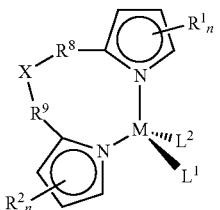

B wherein M is a Group IV metal selected from the group of titanium, zirconium and hafnium, Pyr is pyrrolyl ligand, $R^1$ and $R^2$ can be same or different organic groups substituted at 2,3,4-positions of the pyrrole ring and selected from linear or branched $C_{1-6}$ alkyls, n =1, 2 and 3, $R^8$ and $R^9$ are independently selected from linear or branched chain alkylene group having 2-6 carbon atoms, and X is selected from the group consisting of $CH_2$ and oxygen, alkylamino, dialkyl silyl, and $L^1$ and $L^2$ are independently selected from the group consisting of alkoxide, amide and alkyl, and can be linked together.

13. The film of claim 12, wherein the depositing is selected form the group consisting of a chemical vapor deposition (CVD), cyclic chemical vapor deposition (CCVD), plasma enhanced cyclic chemical vapor deposition, an atomic layer deposition(ALD), and plasma enhanced atomic layer deposition.

14. A semiconductor device containing a thin layer deposited by a precursor comprising at least one metal containing complex with (1) a formula of $(R^1{}_n Pyr)(R^2{}_n Pyr)ML^1 L^2$ having a structure A below:

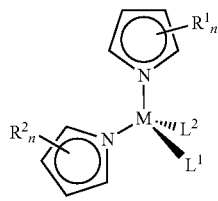

A wherein M is a Group IV metal selected from the group of titanium, zirconium and hafnium, Pyr is pyrrolyl ligand, $R^1$ and $R^2$ can be same or different organic groups substituted at 2,3,4,5-positions of the pyrrole ring and selected from the group consisting of linear or branched $C_{1-6}$ alkyls, and $C_{3-10}$ alkyls containing oxygen or nitrogen atoms; n is 1, 2, 3 or 4, and one of each of $R^1$ and $R^2$ can be linked together via carbon, oxygen, or nitrogen atom;

and $L^1$ and $L^2$ are independently selected from the group consisting of alkoxide, amino and $C_2$-$C_6$ alkyl, and can be linked together;

or (2) a formula of $((R^8 X R^9)(R^1{}_n Pyr)(R^2{}_n Pyr))ML^1 L^2$ having a structure B below:

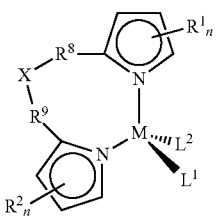

B wherein M is a Group IV metal selected from the group of titanium, zirconium and hafnium, Pyr is pyrrolyl ligand, $R^1$ and $R^2$ can be same or different organic groups substituted at 2,3,4-positions of the pyrrole ring and selected from linear or branched $C_{1-6}$ alkyls, n =1, 2 and 3, $R^8$ and $R^9$ are independently selected from linear or branched chain alkylene group having 2-6 carbon atoms, and X is selected from the group consisting of $CH_2$ and oxygen, alkylamino, dialkyl silyl, and $L^1$ and $L^2$ are independently selected from the group consisting of alkoxide, amide and alkyl, and can be linked together.

15. The film of claim 14, wherein the thin layer is deposited by a depositing method selected form the group consisting of a chemical vapor deposition (CVD), cyclic chemical vapor deposition (CCVD), plasma enhanced cyclic chemical vapor deposition, an atomic layer deposition(ALD), and plasma enhanced atomic layer deposition.

16. The metal containing complex of claim 1, structure A, wherein the $C_{3-10}$ alkyls containing oxygen or nitrogen atoms is selected from the group consisting of —$CH_2CH_2OMe$ and —$CH_2CH_2NMe_2$.

17. The film of claim 12, structure A, wherein the $C_{3-10}$ alkyls containing oxygen or nitrogen atoms is selected from the group consisting of —$CH_2CH_2OMe$ and —$CH_2CH_2NMe_2$.

18. The semiconductor device of claim 14, structure A, wherein the $C_{3-10}$ alkyls containing oxygen or nitrogen atoms is selected from the group consisting of —$CH_2CH_2OMe$ and —$CH_2CH_2NMe_2$.

* * * * *